US008987334B2

(12) United States Patent
Spagnul et al.

(10) Patent No.: US 8,987,334 B2
(45) Date of Patent: Mar. 24, 2015

(54) COSMETIC AND PHARMACEUTICAL FORMULATIONS OF CALIXARENE MOLECULES

(75) Inventors: Aurélie Spagnul, Nice (FR); François Rebiere, Antony (FR); Guillaume Phan, Montrouge (FR); Céline Bouvier-Capely, Chatillon (FR); Elias Fattal, Paris (FR)

(73) Assignee: Institut de Radioprotection et de Surete Nucleaire, Fontenay-aux-Roses (FR)

(*) Notice: Subject to any disclaimer, the term of this patent is extended or adjusted under 35 U.S.C. 154(b) by 94 days.

(21) Appl. No.: 13/140,049

(22) PCT Filed: Dec. 17, 2009

(86) PCT No.: PCT/EP2009/067416
§ 371 (c)(1),
(2), (4) Date: Jun. 16, 2011

(87) PCT Pub. No.: WO2010/070049
PCT Pub. Date: Jun. 24, 2010

(65) Prior Publication Data
US 2011/0281948 A1    Nov. 17, 2011

(30) Foreign Application Priority Data
Dec. 17, 2008    (FR) ...................................... 08 58703

(51) Int. Cl.
| | | |
|---|---|---|
| A01N 37/10 | (2006.01) | |
| A61K 31/19 | (2006.01) | |
| A61Q 19/00 | (2006.01) | |
| A61K 8/362 | (2006.01) | |
| A61K 8/42 | (2006.01) | |

(52) U.S. Cl.
CPC ................ *A61Q 19/00* (2013.01); *A61K 8/362* (2013.01); *A61K 8/42* (2013.01); *Y10S 977/70* (2013.01)
USPC ............................. 514/569; 977/700; 562/466

(58) Field of Classification Search
CPC .......... A61K 8/362; A61K 8/42; A61Q 19/00
USPC ............................. 514/569; 977/700; 562/466
See application file for complete search history.

(56) References Cited

U.S. PATENT DOCUMENTS

| | | | |
|---|---|---|---|
| 5,441,983 A | 8/1995 | Hwang et al. | |
| 5,489,612 A | 2/1996 | Atwood et al. | |
| 2009/0095681 A1* | 4/2009 | Duval et al. .................... | 210/656 |
| 2009/0233941 A1 | 9/2009 | Coleman et al. | |

FOREIGN PATENT DOCUMENTS

| | | |
|---|---|---|
| DE | 103 52 466 A1 | 6/2005 |
| FR | 2 782 007 A1 | 2/2000 |
| FR | 2 899 814 A1 | 10/2007 |
| FR | 2 904 782 A1 | 2/2008 |
| WO | WO 95/19974 A2 | 7/1995 |
| WO | WO 99/24396 A1 | 5/1999 |
| WO | WO 99/55386 A2 | 11/1999 |
| WO | WO 00/07585 A1 | 2/2000 |
| WO | WO 02/44121 A1 | 6/2002 |
| WO | WO 03/024583 A1 | 3/2003 |
| WO | WO 2004/085442 A2 | 10/2004 |
| WO | WO 2005/123660 A2 | 12/2005 |
| WO | WO 2006123051 A2 * | 11/2006 |

OTHER PUBLICATIONS

Henge-Napoli et al, Int. J Radiat. Biol. Nov. 1999; 75(11): 1473-7.*
Fuduka et al, Health Phys. Jul. 2005;89(1):81-8.*
Leyder et al, Tetrahedron 64, 11319-11324, published online Sep. 17, 2008.*
Shinkai et al, J. Am. Chem. Soc. 1987, 109, 6371-6376.*
Souane et al, JNBT, vol. 2, No. 1, pp. 38-41.*
Spagnul et al, Journal of Pharmaceutical Sciences vol. 99, Issue 3, Article first published online: Sep. 24, 2009.*
Leroux, Nature Nanotechnology, vol. 2, Nov. 2007.*
Archimbaud et al., Application of calixarenes for the decorporation of uranium: Present limitations and further trends, Radiation Protection Dosimetry, vol. 53, Nos. 1-4, 1994, pp. 327-330.
Minh et al., "Percutaneous absorption of metallic cations: Particularites of uranium", Ann Pharm Fr 1999, 57, pp. 462-467.
Tymen et al., "Contamination and decontamination of rat and human skin with plutonium and uranium, studied with a Franz's chamber", Int. J. Radiat. Biol., 2000, vol. 76, No. 10, pp. 1417-1424.
Araki et al., "Molecular Design of a Calix[6]arene-Based Super-Uranophile with C3 Symmetry. High UO22+ Selevtivity in Solvent Extraction", Chemistry Letters, 1993, pp. 892-832.
Guo et al., "Retention behavior of dissolved uranium during ultrafiltration: Implications for colloidal U in surface waters", Marine Chemistry, 2007, 107, pp. 156-166.
Guo et al., "Uranium (VI) extraction from chloride solution with benzyloctadecyldimethyl ammonium chloride (BODMAC) in liquid membrane process", Journal of Radioanalytical and Chemistry, 2008, vol. 275, No. 2, pp. 365-369.
Henge-Napoli et al., "Efficacy of ethane-1-hydroxy-1, 1-bisphosphonate (EHBP) for the decorporation of uranium after intramuscular contamination in rats", International Journal of Radiation Biology, 1999, vol. 75, No. 11, pp. 1473-1477.
Houpert et al., "A local approach to reduce industrial uranium wound contamination in rats 1,2", Can. J. Physiol. Pharmacol. 2004, 82, pp. 73-78.
Le Guen et al., "Toxicologie Pathologie professionnelle", Elsevier, 1998, pp. 1-6.
Liu et al., "Formation and stability of paraffin oil-in-water nano-emulsions prepared by the emulsion inversion point method", Journal of Colloid and Interface Science, 2006, 303, pp. 557-563.
Shan et al., "Uranium (VI) extraction by Winsor II microemulsion systems using trialkyl phosphine oxide", Journal of Radioanalytical and Nuclear Chemistry, 2005, vol. 265, No. 3, pp. 419-421.

* cited by examiner

*Primary Examiner* — Wu-Cheng Winston Shen
*Assistant Examiner* — Jean Cornet
(74) *Attorney, Agent, or Firm* — Birch, Stewart, Kolasch & Birch, LLP (57) ABSTRACT

The invention relates to the use of calixarenes for preventing or limiting the transfer of an actinide in the body from a site of skin contamination.

9 Claims, 7 Drawing Sheets

COSMETIC AND PHARMACEUTICAL FORMULATIONS OF CALIXARENE MOLECULES

The invention relates to the field of treatments for cutaneous actinide contamination.

Each year, nuclear industry activities require the handling of tens of thousands of tons of uranium during the various stages of nuclear fuel processing: extraction from uranium mines, chemical purification, enrichment, manufacture of combustible elements, reprocessing of irradiated fuel and monitoring of its storage. Uranium or transuranic actinides (plutonium or americium, for example) are thus handled in facilities involved in the fuel cycle, but also in research laboratories working upstream as well as downstream from the cycle.

In order to ensure the protection of nuclear sector workers, exposure to the ionizing radiation associated with a given protocol must be as low as possible. To this end, sites of potential exposure are subject to significant technical constraints that ensure monitoring of external exposure to irradiation (γ alarm beacons, individual dosimeters) as well as internal contamination (aerosol sampling devices, pulmonary whole-body radiometry, urinary and fecal uranium assays) of potentially exposed workers [1]. However, in spite of the protective means implemented in the working environment, a certain number of nuclear worker exposure accidents are recorded. The principal routes by which actinides become incorporated in the body are inhalation, ingestion and the cutaneous route (surface contamination and/or wound).

Contamination via wound remains very worrying since it can cause significant and long-lasting internal contamination of individuals after the actinides are transferred into the body. Indeed, in the case of accidental injury involving contamination by actinides such as soluble uranium compounds, the transfer of actinides through abraded skin, and thus resorption by circulating blood, can occur very quickly (30 minutes). Moreover, if the decontamination of a superficial wound is only partial, the uranium remains biologically available because the viable epidermis behaves like a reservoir of uranium [2]. Thus, early cytotoxic effects are observed in the skin. The uranium then passes through the body via systemic circulation and a first portion of the uranium is eliminated by urinary excretion. The quantity of radioelement remaining in the body settles in two principal target organs, namely the kidneys and the skeleton. Differential effects can then appear in these organs, thus showing the long-term chemical and radiological toxicity of uranium, notably in the case of the most active compounds (enriched uranium) [2-4].

Current methods of cutaneous decontamination involve, after transferring the individual to a medical facility, cleaning the skin using a suitable disinfecting solution supplemented with a chelating agent, such as 25% diethylene triamine pentaacetic acid (DTPA), for example, in the case of wounds. Wound cleaning can then be supplemented by surgical excision of contaminated tissue in the case of contamination by particles. In the case of soluble uranium compounds, it is important to emphasize that the period of time between the moment of contamination and arrival at the medical facility (15 minutes on average) is sufficient to allow uranium to diffuse through the corneal layer of the skin, which leads to the formation of a reservoir of uranium which can then diffuse more deeply [5].

However, there is no alternative emergency measure for satisfactorily preventing or limiting the transfer of actinides through a wound at the moment and site of an accident. Moreover, the chelating agents available in medical facilities, such as DTPA, are not able to selectively complex with uranium compounds and their effectiveness remains very limited in a biological environment.

The therapy of choice in the case of internal contamination by actinides next consists in injecting in the victim by systemic route solutions containing decorporation agents which accelerate the urinary elimination of incorporated actinides (e.g., DTPA solution for Pu and Am). Since a DTPA solution is not effective for uranium decorporation, other potentially effective decorporation agents such as catecholate (CAM) and hydroxypyridinonate (HOPO) ligands have been proposed, but are not yet clinically accepted [6, 7]. The ligand ethane-1-hydroxy-1,1-bisphosphonate (EHBP) is found to be as good a uranium complexing agent as HOPO and CAM and has the advantage of already being used clinically in other indications [8]. However, the decorporating action of these agents strongly depends on the time passed between the moment of contamination and the injection [8].

Finally, the absence of an emergency measure to administer at the moment and site of an accident constitutes a gap which is advisable to fill in order to limit the potential penetration of actinides in the body from the wound or from the surface of cutaneous contamination. The search for a decontamination agent aimed at reducing the transcutaneous flow of actinides following contamination by contact or by wound is a subject of topical interest for which relatively little work has been carried out [3, 4, 9-11].

Application WO 2006/123051 describes the use of p-tert-butylcalix[6]arenes bound to a support to selectively complex uranium, americium and plutonium in urine.

Application WO 95/19974 describes the use of calix[3-8]arenes for treating bacterial or fungal infections, HIV and cancer.

Calixarenes are distinctive complexing cages. In 1993, Araki et al. showed the complexing properties, in liquid-liquid extraction, of 1,3,5-O-trimethyl-2,4,6-O-tri(carboxylic acid)-para-tert-butylcalix[6]arene (molecule represented hereinafter by formula IA) with respect to uranium (Chem. Lett., 829-832, 1993). In 1994, Van Duynhoven et al. used the same molecule to study its conformational equilibria (J. Am. Chem. Soc., 116, 5814-5822). In 1997, C. Dinse et al. (Radioprotection, 32 no. 5, 659-671) showed the selectivity, in liquid-liquid extraction, of the molecule of the formula (IA) below with respect to uranium in the presence of plutonium and sodium.

None of the products or techniques of the prior art makes it possible to propose an emergency topical measure to limit or to stop the penetration in the body of actinides from cutaneous contamination.

In an unexpected manner, the inventors have shown that an oil-in-water nanoemulsion comprising p-tert-butylcalix[6]arenes in the oil phase makes it possible to bind uranium and to prevent its transdermal diffusion.

The present invention thus relates to a calixarene, preferably a calix[6]arene, for the use thereof for treating cutaneous actinide contamination.

Advantageously, the inventive calixarene is a para-tert-butylcalix[6]arene of the formula (IA) or (IB):

wherein R1, R3 and R5, identical or different, each independently represent:

(i) a hydrogen or halogen atom, (ii) an acetyl, amino, phosphate, nitro, sulfate, carboxy, carboxylic, thiocarboxy, carbamate or thiocarbamate radical, (iii) an optionally substituted linear or branched alkyl having 1 to 60, preferably 1 to 30, carbon atoms which optionally exhibits at least one ethylenic or acetylenic unsaturation, (iv) an optionally substituted cycloalkyl having from 3 to 12 carbon atoms which optionally exhibits at least one ethylenic or acetylenic unsaturation, (v) an optionally substituted aryl, an optionally substituted naphthyl, an optionally substituted aryl($C_1$-$C_{30}$ alkyl) or an optionally substituted ($C_1$-$C_{30}$ alkyl)aryl, it being possible for the radicals (ii) to (v) to be substituted by halogen atoms, organometallic compounds, alcohol, amine, carboxylic, sulfonic, sulfuric, phosphoric, phosphoric or hydroxamic acid or ester, carbamate, thiocarbamate, ether, thiol, epoxide, thioepoxide, isocyanate or isothiocyanate functional groups or it being possible for a carbon of these radicals to be replaced by a nitrogen, sulfur, phosphorus, oxygen, boron or arsenic heteroatom, (vi) a polysaccharide.

According to an advantageous embodiment, in formulae (IA) and (IB), two from R1, R3 and R5 represent hydrogen or methyl, the third being a polysaccharide.

Advantageously, said polysaccharide is selected from the group comprised of dextrans, chitosan and agaroses.

According to another advantageous embodiment, the inventive para-tert-butylcalix[6]arenes are compounds of the formula (IA) or (IB) wherein R1, R3 and R5 are identical and preferably represent hydrogen.

The present invention also relates to the use of a calixarene for preparing a drug for treating cutaneous actinide contamination.

The present invention also relates to a method for treating cutaneous actinide contamination comprising the application on the skin of an effective quantity of calixarene.

The chemical series of actinides comprises the chemical elements of the periodic table located between actinium and lawrencium, thus having an atomic number between 89 and 103 inclusive, namely actinium (Ac), thorium (Th), protactinium (Pa), uranium (U), neptunium (Np), plutonium (Pu), americium (Am), curium (Cm), berkelium (Bk), californium (Cf), einsteinium (Es), fermium (Fm), mendelevium (Md), nobelium (No) and lawrencium (Lr).

All actinides are radioactive elements and take their name from actinium (Z=89), a heavy metal, because they have similar chemical properties.

The actinide produced most abundantly in the nuclear fuel cycle is plutonium, primarily its principal isotope plutonium-239, which is itself fissile. But nuclear reactors generate, in smaller quantities, other actinides, which are called "minor" actinides for this reason. The principal ones are neptunium-237, americium-241, americium-243, curium-244 and curium-245. The minor actinides constitute with fission products most high-activity, long-lived radioactive waste, i.e., the nuclear industry's most dangerous waste.

Advantageously, the invention is used for treating cutaneous contamination by uranium, plutonium and/or americium.

The present invention also relates to the use of calixarenes, advantageously calix[6]arenes, for preventing or limiting the transfer of an actinide into the body from a cutaneous contamination site, advantageously for preventing or limiting the transfer of uranium, plutonium and/or americium into the body from a cutaneous contamination site.

Indeed, the invention provides a dermocosmetic composition for preventing the penetration of actinides into the body from a cutaneous contamination site or for limiting the quantity of actinide penetrating into the body to a quantity insufficient to trigger a symptom related to contamination, in particular a kidney or bone symptom.

The present invention also relates to a dermocosmetic composition comprising one or more calixarene compounds as an active ingredient and one or more cosmetically acceptable excipients.

The term "dermocosmetic composition" means a cosmetic composition intended for application on the skin.

The present invention also relates to a dermatological composition comprising one or more calixarene compounds as an active ingredient and one or more pharmaceutically acceptable excipients.

The term "dermatological composition" means a pharmaceutical composition intended for application on the skin.

Advantageously, the excipients of the inventive formulation are selected in conformity with the French Pharmacopeia.

Advantageously, the excipients of the inventive dermocosmetic or dermatological formulation do not constitute promoters of cutaneous penetration which could disrupt the cutaneous structure and promote the cutaneous penetration of contaminant actinides.

Given the strong lipophilic character of calixarene molecules, the inventive dermocosmetic or dermatological composition is advantageously provided in a form comprising an oil phase, wherein the calixarene compounds are in the oil phase, such as:
- an oil-based gel;
- an anhydrous paste whose base is a solid fat phase or a wax;
- an oil-in-water (O/W) emulsion comprised of the dispersion of oil droplets in water or a water-in-oil (W/O) emulsion comprised of the dispersion of water droplets in the oil phase.

Advantageously, the inventive dermocosmetic or dermatological composition is an oil-in-water or water-in-oil nanoemulsion, preferably an oil-in-water nanoemulsion.

The term "nanoemulsion" refers to an emulsion whose droplet size is between 50 nm and 200 nm.

The emulsion, and in particular the nanoemulsion (mean diameter of dispersed droplets less than one micron), has proven to be a particularly advantageous formulation because it exhibits relatively low persistence and is therefore easily washable, thus enabling more effective decontamination. Moreover, it is likely to ensure better availability of the calixarenes at the skin surface and has a large total developed surface by virtue of the oil droplets finely dispersed in the aqueous phase.

Advantageously, the inventive dermocosmetic or dermatological composition in nanoemulsion form has droplets between 50 nm and 200 nm in size, preferentially between 100 nm and 200 nm in size.

Advantageously, the oil phase is comprised of mineral oils, vegetable oils, synthetic oils or a mixture thereof. Preferentially, the oil phase includes paraffin. In a particularly preferred manner, the oil phase consists of paraffin.

Advantageously, at least one of the calix[6]arene compounds present in the inventive dermatological composition as an active ingredient is of the formula (IA) or (IB) as previously defined wherein R1, R3 and R5 are as previously defined.

Preferentially, all the calix[6]arene compounds present in the inventive dermatological composition as an active ingredient are of the formula (IA) or (IB) as previously defined wherein R1, R3 and R5 are as previously defined.

Preferentially, the inventive dermatological composition comprises 50% to 95% water, preferentially 70% to 80% water. Preferentially, the inventive dermatological composition comprises 5% to 50% oil phase, preferentially 15% to 25% oil phase. Preferentially, the inventive dermatological composition comprises 1% to 15% surfactants. Advantageously, the inventive dermatological composition comprises 2 mg to 30 mg, preferably 2 mg to 12 mg, calix[6]arene per gram of the composition. When the inventive dermatological composition is a nanoemulsion, said composition comprises 2 mg to 30 mg, preferably 2 mg to 12 mg, calix[6]arene per gram of the composition.

Advantageously, at least one of the calixarene compounds present in the inventive dermocosmetic composition is a calix[6]arene.

Preferentially, all the calixarene compounds present in the inventive dermocosmetic composition as an active ingredient are calix[6]arenes.

Advantageously, at least one of the calixarene compounds present in the inventive dermocosmetic composition as an active ingredient is of the formula (IA) or (IB) as previously defined wherein R1, R3 and R5 are as previously defined.

Preferentially, all the calixarene compounds present in the inventive dermocosmetic composition as an active ingredient are of the formula (IA) or (IB) as previously defined wherein R1, R3 and R5 are as previously defined.

Preferentially, the inventive dermocosmetic composition comprises 50% to 95% water, preferentially 70% to 80% water. Preferentially, the inventive dermocosmetic composition comprises 5% to 50% oil phase, preferentially 15% to 25% oil phase. Preferentially, the inventive dermocosmetic composition comprises from 1% to 15% surfactants. Advantageously, the inventive dermocosmetic composition comprises 2 mg to 30 mg, preferably 2 mg to 12 mg, calixarene per gram of the composition. When the inventive dermocosmetic composition is a nanoemulsion, said composition comprises 2 mg to 30 mg, preferably 2 mg to 12 mg, calixarene per gram of the composition.

The following examples illustrate the invention without limiting its scope.

EXAMPLES

Example 1

Preparation of an Oil-in-Water Nanoemulsion of calix[6]arene

An oil-in-water nanoemulsion is prepared, wherein the calixarene molecules are incorporated in the oil phase. Said nanoemulsions are comprised of mineral oil (paraffin oil), nonionic surfactants (Tween 80® and Span 80®), Milli-Q water and 1,3,5-O-Me-2,4,6-OCH$_2$COOH-p-tert-butylcalix[6]arene. The mass percentages of surfactants, oil and water were set at 5%, 20% and 75%, respectively. The relative mass percentages of the two surfactants were optimized in order to obtain optimum emulsification conditions (hydrophilic-lipophilic balance (HLB)=11).

Figure 1:
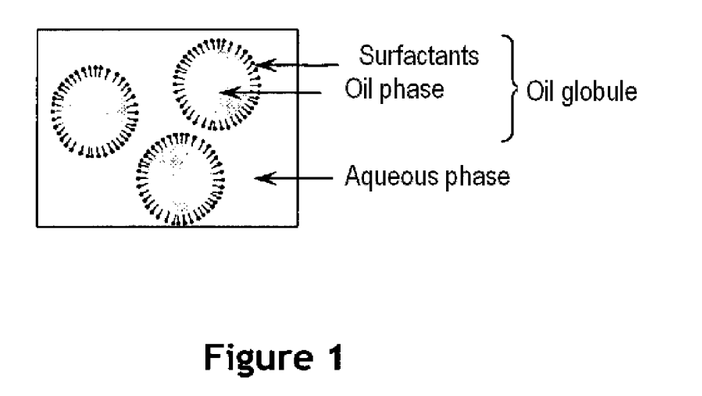
FIG. 1: Diagram of an oil-in-water emulsion.
Figure 2:
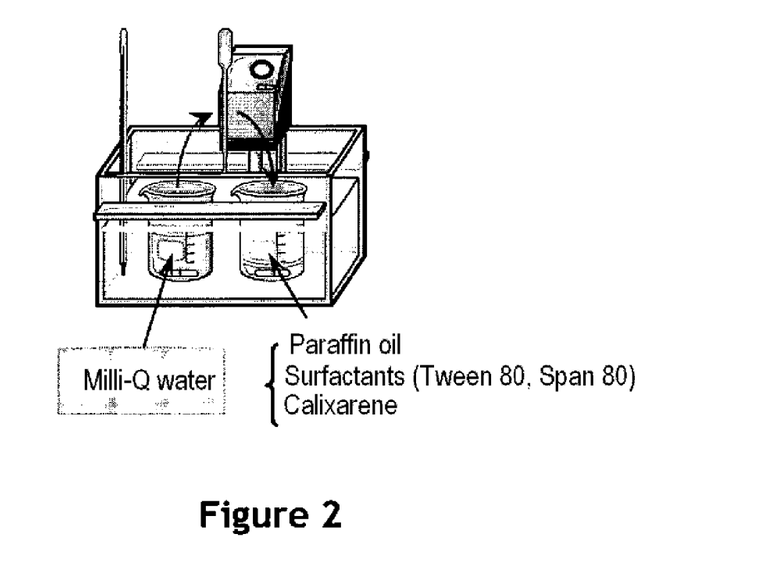
FIG. 2: Embodiments of nanoemulsions.

Calixarene nanoemulsions were prepared according to the phase inversion method. The oil phase of the emulsion corresponding to the oil-calixarene-surfactants mixture and the aqueous phase are first placed separately in a 50° C. temperature-controlled bath with gentle agitation for 30 minutes. At the end of this temperature equilibration period, the aqueous phase is added drop wise to the oil phase under gentle agitation (FIG. 2). The nanoemulsions thus obtained are kept under agitation in the temperature-controlled bath for 45 minutes and then are agitated at room temperature for 45 minutes. The nanoemulsions are then kept at room temperature away from light.

Example 2

Characterization of Nanoemulsions Obtained in Example 1

The nanoemulsions were characterized by measuring dispersed oil droplet size, zeta potential (total surface charge that the droplets acquire in the aqueous medium) and pH. Emulsion direction was also verified by conductometry and the test of emulsion dilution in water.

The mean size of the dispersed oil droplets and the polydispersity index (PDI) reflecting size distribution homogeneity were measured by photon correlation spectroscopy.

Figure 3:
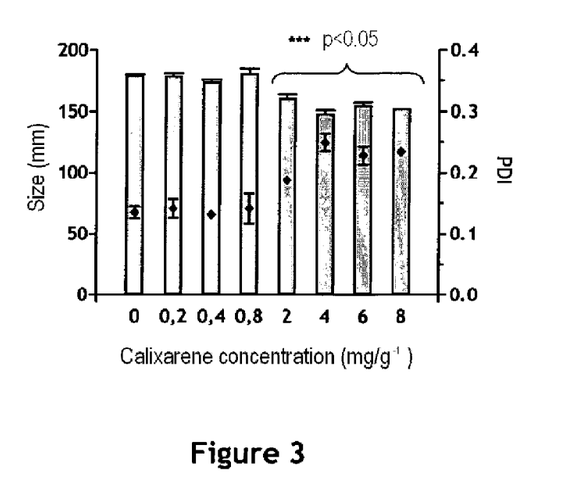
FIG. 3: Changes in dispersed oil droplet size as a function of calixarene concentration in nanoemulsions.

This study showed that the diameter of the oil globules is less than 200 nm and that it decreases significantly (p<0.05) when the quantity of calixarene introduced is greater than 2 mg per gram of emulsion (FIG. 3). This decrease in size is correlated with a significant (p<0.05) increase in the polydispersity index, thus reflecting a decrease in emulsion homogeneity. However, the PDI value remains small (<0.250), which indicates that the oil droplet size distribution remains homogeneous for nanoemulsions loaded with up to 8 mg/g calixarene.

Zeta potential was determined by measuring the electrophoretic mobility of dispersed oil globules.

Figure 4:
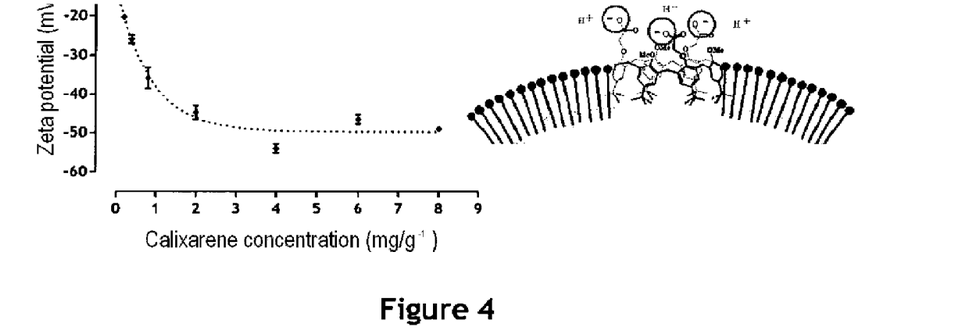
FIG. 4: Changes in zeta potential of oil droplets as a function of calixarene concentration in the emulsion (A). Hypothesis of calixarene molecule localization on the surface of oil droplets of the emulsion (B).

This measurement demonstrated the presence of calixarene at the surface of these droplets (FIG. 4). Indeed, the increase in calixarene concentration in the nanoemulsions results in a decrease in the surface charge of the oil droplets up to a concentration of 4 mg/g, a concentration beyond which zeta potential tends to stabilize. This stabilization can be explained by a probable deprotonation of calixarene molecules found on the surface of the oil globules.

Figure 5:
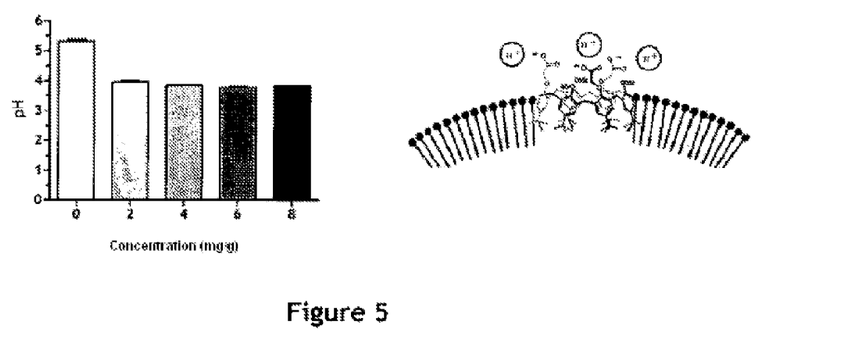
FIG. 5: Changes in pH of emulsions as a function of the incorporated calixarene concentration (A). Hypothesis of calixarene molecule localization on the surface of oil droplets of the emulsion (B).

The presence of calixarene on the surface of the dispersed oil droplets was also demonstrated by measuring pH. A comparison of the pH of emulsions not loaded with calixarene and emulsions loaded with 2 mg/g, 4 mg/g, 6 mg/g and 8 mg/g calixarene showed a decrease in pH of approximately one unit in the presence of the chelating agent. This phenomenon is explained by deprotonation of calixarene molecules present on the surface of the oil globules (FIG. 5).

Example 3

In Vitro Effectiveness of Calixarene Nanoemulsions for Decontamination

Effectiveness of the calixarene nanoemulsions was evaluated in vitro using the ultrafiltration technique. Indeed, ultrafiltration makes it possible to recover part of the aqueous phase of nanoemulsions after which it is possible to assay free uranium using inductively coupled plasma mass spectrometry (ICP-MS).

First, the ultrafiltration-ultracentrifugation parameters were optimized in order to obtain in the filtrate only the nanoemulsion aqueous phase:
filter porosity: 3000 kDa
volume to be centrifuged: 400 μl
centrifugation temperature: 20° C.
centrifugation speed: 6000 rpm
centrifugation duration: 30 min The limpid filtrates thus obtained were analyzed by high-performance liquid chromatography (HPLC). HPLC analysis showed that the filtrates consist of water only, thus indicating the absence of oil, surfactants or calixarene.

Figure 6:
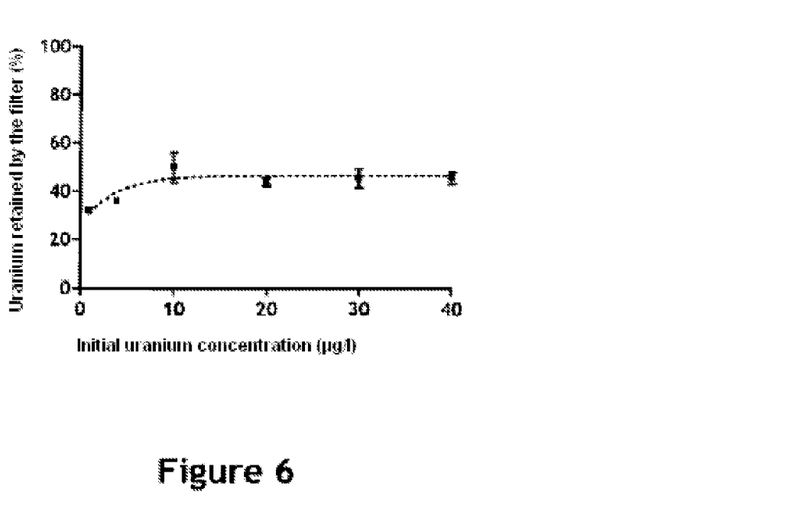
FIG. 6: Percentage of uranium retained by the ultrafiltration system filter as a function of deposited uranium concentration.
Figure 7:
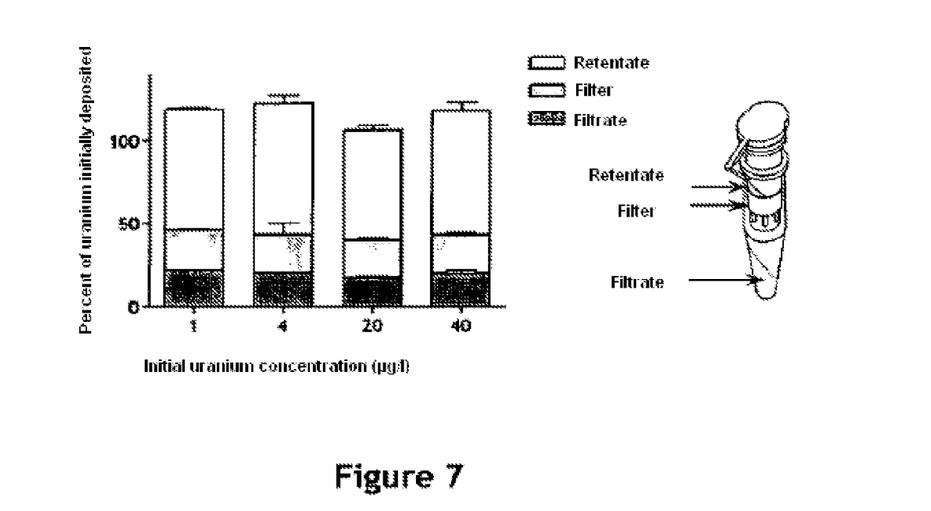
FIG. 7: Distribution of uranium between retentate, filter and filtrate after ultrafiltration (A). Representation of the ultrafiltration system (B).

A study aimed at evaluating uranium retention by filters used in ultrafiltration was then undertaken. This study led to the conclusion that 47% on average of the uranium deposited on the filter in the form of uranyl nitrate in acetate buffer, pH 5, is retained in the filter during ultrafiltration (FIG. 6). This is due to the fact that the filter consists of regenerated cellulose, a material that has negatively charged sites with which uranium can interact via electrostatic bonds and can thus be retained [16]. That this percentage corresponded well to uranium retained in the filter and not to a phenomenon of uranium concentration in the phase deposited on the filter (retentate) was also verified by evaluating the components (FIG. 7). Indeed, there is no increase in uranium concentration in the retentate after ultrafiltration compared to the concentration initially deposited.

Knowing that by using the ultrafiltration technique it is possible to recover nanoemulsion filtrates comprised only of water and that 47% on average of the uranium is retained by the ultrafiltration system filter, it is thus possible to evaluate in vitro the decontamination capacity of calixarene nanoemulsions.

This calixarene nanoemulsion decontamination effectiveness test was carried out according to two modes of contact between contaminant and nanoemulsion:
- dynamic contact: agitation by inversion for a given length of time of a test tube containing the contaminant solution and the calixarene nanoemulsion,
- static contact: placing the calixarene nanoemulsion in contact with the contaminant solution for a given length of time without agitation.

The extraction kinetics of uranium by the calixarene nanoemulsions could be thus determined (with the following ratios: $Q_{calixarene}/Q_{uranium}=10000$ and $V_{contamination}/V_{formulation}=1$ (FIG. 8)).

Figure 8:
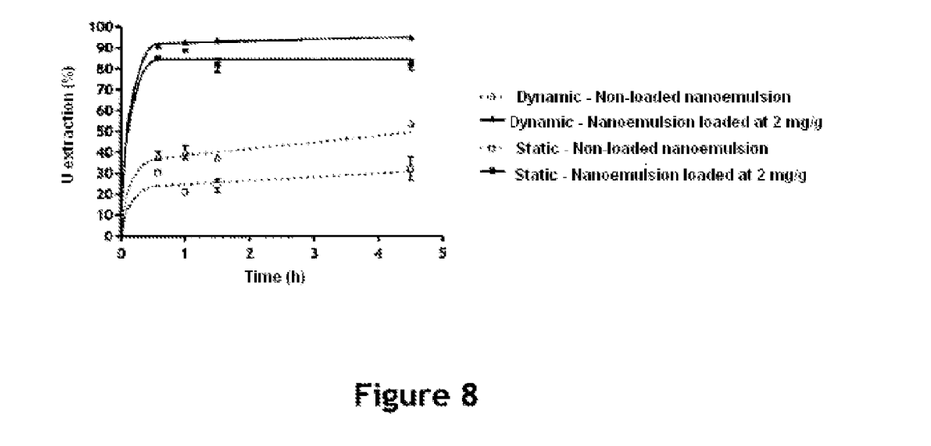
FIG. 8: Percentage of uranium extracted as a function of contact time between contaminant solution and nanoemulsion and as a function of contact type (dynamic and static). Note: contact time represented=actual experimentation time+30 minutes of ultrafiltration.

This study shows that the nanoemulsions not loaded with calixarene extract approximately 25% of the uranium in static mode and 40% in dynamic mode. This can be explained by the trapping of uranium by nonionic surfactants, because the latter have ethoxyl groups capable of establishing hydrogen bonds with hydroxyl ions [17] and thus also capable of retaining uranium. Agitating the nanoemulsion mixture not loaded with calixarene and the contaminant solution promotes contact between the uranium and the surfactants, which can explain why uranium extraction is greater under dynamic conditions.

Concerning the nanoemulsions loaded with 2 mg/g calixarene, roughly 90% of the uranium is extracted after 35 minutes (5 minutes of actual experimentation time) in dynamic mode compared to roughly 85% in static mode. These results thus show that the presence of calixarene in the nanoemulsions improves by at least a factor of two the uranium extraction yield.

Figure 9:
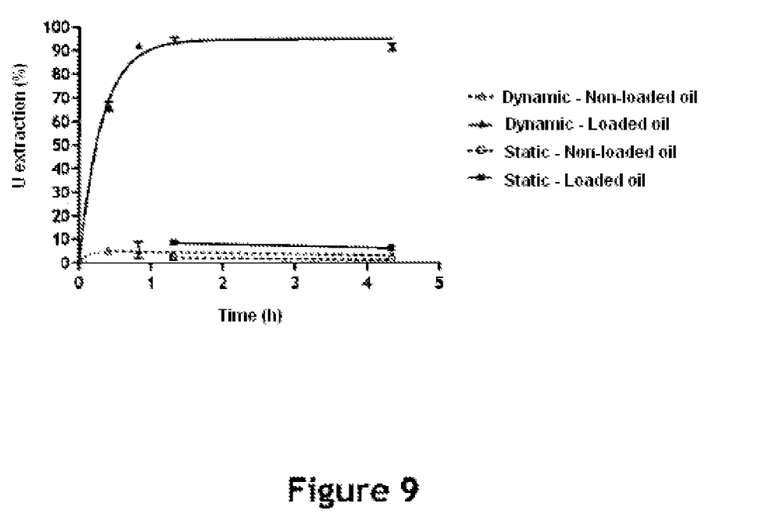
FIG. 9: Percentage of uranium extracted as a function of contact time between contaminant solution and calixarene dispersion in paraffin oil and as a function of contact type (dynamic and static). Note: contact time represented=actual experimentation time+20 minutes of treatment.

Moreover, a kinetics study previously carried out with paraffin oil loaded with calixarene as a galenic formulation showed that less than 10% of the uranium was extracted by this formulation in static mode, all other conditions remaining equal ($Q_{calixarene}/Q_{uranium}=10000$ and $V_{contamination}/V_{formulation}=1$, (FIG. 9)).

It is thus clear that the selected formulation (calixarene nanoemulsion) is much more effective than the excipient (paraffin oil) alone loaded with calixarene. This is most probably due to the fact that the surface developed between calixarene and uranium in the nanoemulsions is much larger.

In conclusion, these results show that the selected formulation (nanoemulsion) and the active ingredient used, i.e., calixarene, contribute to the effectiveness of the galenic form. Calixarene nanoemulsions are thus effective in static decontamination. They are thus systems well suited to wound decontamination.

Example 4

Ex Vivo Effectiveness of Calixarene Nanoemulsions for Decontamination

Figure 10:
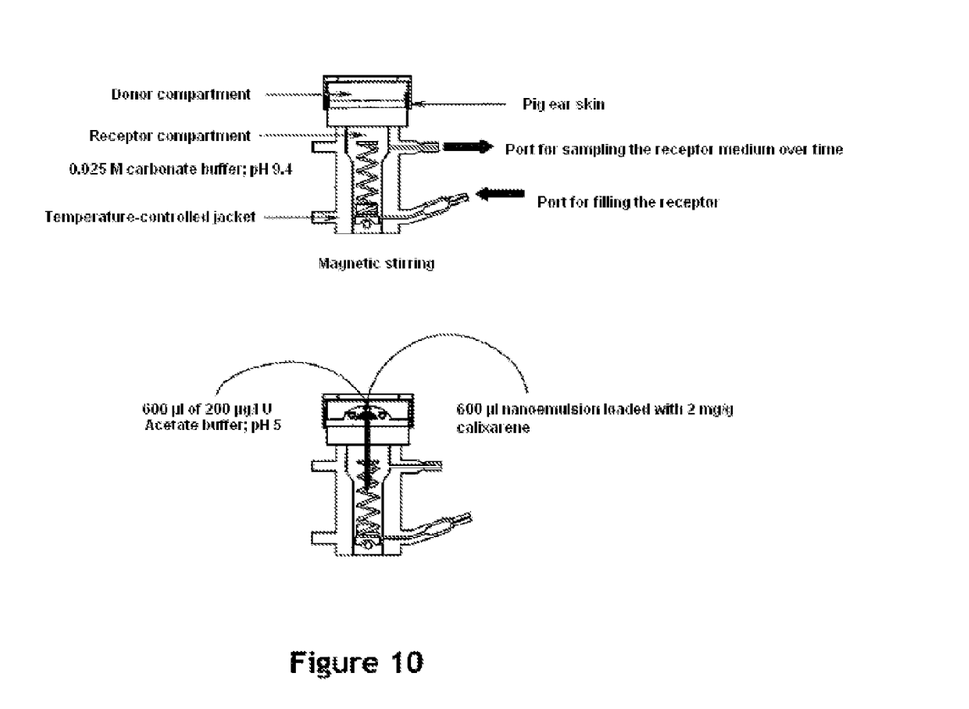
FIG. 10: Diagrams of Franz cells used to study transcutaneous passage of uranium or calixarene molecules from formulations.

The effectiveness of calixarene nanoemulsions was evaluated using a Franz cell system by studying the transcutaneous passage kinetics of uranium with and without application of nanoemulsion (FIG. 10). All the transdermal diffusion studies were undertaken on pig ear skin explants in occlusive conditions (n=5). The contamination was carried out by depositing a solution of depleted uranium ($^{238}U$) in acetate buffer, pH 5.

A first experiment aimed at determining the transcutaneous passage kinetics of calixarene released from 1 ml nanoemulsion loaded with 4 mg/g calixarene showed that the calixarene thus formulated did not pass through the skin during an exposure period of 24 hours (HPLC detection with a λ wavelength=210 nm: limit of detection (LD)=17 ng/ml; limit of quantification (LQ)=52 ng/ml).

The study of the decontamination effectiveness of a nanoemulsion loaded with 4 mg/g carboxylic calixarene ($Q_{calixarene}/Q_{uranium}$ ratio=10000) demonstrated a 98% decrease in the quantity of uranium diffused through the skin after 24 hours.

Figure 11:
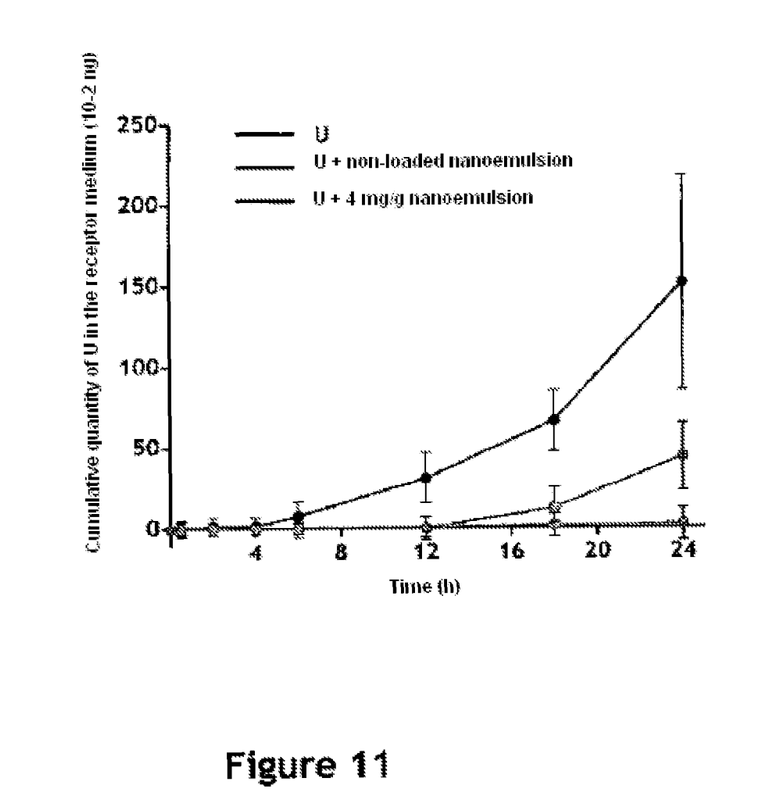
FIG. 11: Transcutaneous diffusion kinetics of uranium over 24 hours in a Franz cell (n=5), in the absence or presence of calixarene nanoemulsion.

Indeed, treating contamination by depositing a nanoemulsion not loaded with calixarene already enables a 71% decrease in the quantity of diffused uranium. This is due in part to the dilution of uranium in the aqueous phase of the emulsion and in part to the trapping of a portion of the uranium by the components of the nanoemulsion (shown in the in vitro tests). Adding calixarene to the nanoemulsion further decreases by 93% the quantity of uranium diffused compared to the nanoemulsion not loaded with calixarene (FIG. 11).

In conclusion, these results confirm the effectiveness of calixarene nanoemulsions for decontaminating skin contaminated by uranium, as said calixarene nanoemulsions reduce the transcutaneous transfer of said actinide.

REFERENCES

[1] Le Guen B and Bérard P. Uranium et ses composés. In: Toxicologie-Pathologie professionnelle, Paris; Elsevier, 1998, Encyclopédie Médico Chirurgicale 16-008-10.

[2] Petitot F, Moreels A M and Paquet F. In vitro evaluation of percutaneous diffusion of uranyl nitrate through intact or excoriated skin of rat and pig. *Can J Physiol Pharmacol* 82 (2):133-9 (2004).

[3] Tymen H, Gerasimo P and Hoffschir D. Contamination and decontamination of rat and human skin with plutonium and uranium, studied with a Franz's chamber. *Int J Radiat Biol* 76 (10):1417-24 (2000).

[4] Tymen H, Rateau G, Guillet K, Ramounet-Le Gall B, Gerasimo P and Fritsch P. Methods to measure transfer of radionuclides through intact or injured skin: Application to radiotoxicology. *Canadian Journal of Physiology and Pharmacology* 80 (7):733-741 (2002).

[5] De Rey B M, Lanfranchi H E and Cabrini R L. Percutaneous absorption of uranium compounds. *Environmental Research* 30 (2):480-491 (1983).

[6] Durbin P W, Kullgren B, Xu J and Raymond K N. Development of decorporation agents for the actinides. *Radiation Protection Dosimetry* 79 (1-4):433-443 (1998).

[7] Fukuda S, Lida H, Ikeda M, Yan X and Xie Y. Toxicity of uranium and the removal effects of CBMIDA and EHBP in simulated wounds of rats. *Health Phys* 89 (1):81-8 (2005).

[8] Henge-Napoli M H, Ansoborlo E, Chazel V, Houpert P, Paquet F and Gourmelon P. Efficacy of ethane-1-hydroxy-1,1-bisphosphonate (EHBP) for the decorporation of uranium after intramuscular contamination in rats. *Int J Radiat Biol* 75 (11):1473-7 (1999).

[9] Houpert P, Chazel V, Paquet F, Bailly T, Burgada R and Henge-Napoli M H. Reduction of uranium transfer by local chelation in simulated wounds in rats. *Hum Exp Toxicol* 20 (5):237-41 (2001).

[10] Houpert P, Chazel V and Paquet F. A local approach to reduce industrial uranium wound contamination in rats. *Can J Physiol Pharmacol* 82 (2):73-8 (2004).

[11] Yang Z, Xu K, Wang L, Gu H, Wei H, Xang M and Xu B. Self-assembly of small molecules affords multifunctional supramolecular hydrogels for topically treating simulated uranium wounds. *Chem Commun* 35:4414-4416 (2005).

[12] Shan Z, Yang Y-Z, Tao Z, Jian H and Chang-Hong L. Uranium(VI) extraction by Winsor microemulsion systems using trialkyl phosphine oxide. *Journal of Radioanalytical and Nuclear Chemistry* 265 (3):419-421 (2005).

[13] Guo J-x, Sun X, Du D-I, Wu X, Li M-x, Pang H, Sun S-x and Wang A-h. Uranium(VI) extraction from chloride solution with benzyloctadecyldimethyl ammonium chloride (BODMAC) in a liquid membrane process. *Journal of Radioanalytical and Nuclear Chemistry* 275 (2):365-369 (2008).

[14] Seiller M and Martini M C. Formes pharmaceutiques pour application locale. Lavoisier, 1996.

[15] Martini M-C. Introduction à la dermopharmacie et à la cosmétologie. Lavoisier 2006, p. 411.

[16] Guo L, Warnken K W and Santschi P H. Retention behavior of dissolved uranium during ultrafiltration: Implications for colloidal U in surface waters. *Marine Chemistry* 107 (2):156-166 (2007).

[17] Liu W, Sun D, Li C, Liu Q and Xu J. Formation and stability of paraffin oil-in-water nano-emulsions prepared by the emulsion inversion point method. *Journal of Colloid and Interface Science* 303 (2):557-563 (2006).

The invention claimed is:

1. A method for the treatment of cutaneous actinide contamination comprising topically administering to a person in need thereof calix[6]arene in the form of an oil-in-water or water-in-oil nanoemulsion composition.

2. The method of claim 1 wherein the calix[6]arene is represented by formula (IA) or (IB):

wherein R1, R3 and R5, identical or different, each independently represent:
 (i) a hydrogen or halogen atom,
 (ii) an acetyl, amino, phosphate, nitro, sulfate, carboxy, carboxylic, thiocarboxy, carbamate or thiocarbamate radical,
 (iii) an optionally substituted linear or branched alkyl having 1 to 60 carbon atoms which optionally exhibits at least one ethylenic or acetylenic unsaturation,
 (iv) an optionally substituted cycloalkyl having from 3 to 12 carbon atoms which optionally exhibits at least one ethylenic or acetylenic unsaturation,
 (v) an optionally substituted aryl, an optionally substituted naphthyl, an optionally substituted aryl($C_1$-$C_{30}$ alkyl) or an optionally substituted ($C_1$-$C_{30}$ alkyl)aryl,
 it being possible for the radicals (ii) to (v) to be substituted by halogen atoms, organometallic compounds, alcohol, amine, carboxylic, sulfonic, sulfuric, phosphoric, phosphonic or hydroxamic acid or ester, carbamate, thiocarbamate, ether, thiol, epoxide, thioepoxide, isocyanate or isothiocyanate functional groups or it being possible for a carbon of these radicals to be replaced by a nitrogen, sulfur, phosphorus, oxygen, boron or arsenic heteroatom, or
 (vi) a polysaccharide.

3. The method of claim 2, wherein the optionally substituted linear or branched alkyl of (iii) has 1 to 30 carbon atoms which optionally exhibits at least one ethylenic or acetylenic unsaturation.

4. The method of claim 1, wherein the calix[6]arene is in the form of an oil-in-water or water in oil nanoemulsion composition.

(IA)

(IB)

5. The method of claim 2, wherein the calix[6]arene is in the form of an oil-in-water nanoemulsion composition.

6. The method of claim 1, wherein said cutaneous actinide contamination is by uranium, plutonium and/or americium.

7. The method of claim 1, wherein the nanoemulsion composition contains droplets between 100 nm and 200 nm in size.

8. The method of claim 1, wherein said nanoemulsion composition comprises:
2 mg to 30 mg of calix[6]arene per gram of the nanoemulsion composition;
50% to 95% of water;
5% to 50% of oil phase; and
1 to 15% of one or more surfactants.

9. The method of claim 8, wherein the nanoemulsion composition contains droplets between 100 nm and 200 nm in size.

* * * * *